United States Patent [19]

Ohashi

[11] Patent Number: 5,354,679
[45] Date of Patent: Oct. 11, 1994

[54] MICROORGANISM IMMOBILIZATION IN A β-CHITIN CARRIER

[75] Inventor: Eiji Ohashi, Tokyo, Japan

[73] Assignee: Nippon Suisan Kaisha, Ltd., Tokyo, Japan

[21] Appl. No.: 904,258

[22] Filed: Jun. 25, 1992

[30] Foreign Application Priority Data

Jun. 25, 1991 [JP] Japan .................. 3-153268

[51] Int. Cl.$^5$ ............. C12N 11/10; C12N 11/04; C12M 1/40; G01N 27/26
[52] U.S. Cl. ............. 435/178; 204/403; 435/182; 435/288; 435/817
[58] Field of Search ............. 435/178, 182, 817, 288; 204/403

[56] References Cited

U.S. PATENT DOCUMENTS

| | | | |
|---|---|---|---|
| 4,089,746 | 5/1978 | Masri et al. | 435/178 |
| 4,167,447 | 9/1979 | Masri et al. | 435/178 |
| 4,415,666 | 11/1983 | Orazio et al. | 435/179 |
| 4,931,551 | 6/1990 | Albisetti | 514/55 X |
| 4,958,012 | 9/1990 | Tokura et al. | 536/20 |

FOREIGN PATENT DOCUMENTS

| | | |
|---|---|---|
| 53-10151 | 4/1978 | Japan . |
| 56-00035 | 1/1981 | Japan . |
| 61-53339 | 3/1986 | Japan . |
| 61-64256 | 4/1986 | Japan . |
| 61-111686 | 5/1986 | Japan . |
| 61-129005 | 6/1986 | Japan . |
| 61-212302 | 9/1986 | Japan . |

OTHER PUBLICATIONS

Ohashi et al.; "Simple and mild preparation of an enzyme-immobilized membrane for a biosensor using β-type crystalline chitin"; Analytica Chimica Acta; vol. 262, No. 1; 1992; pp. 19–25.

Kovalenko et al.; "Enzyme-based glucose analyzers"; 2357 Journal of Analytical Chemistry USSR; 44(1989) Mar., No. 3, Part 1; pp. 307–316.

Portier; "Chitin immobilization systems for hazardous waste detoxification and biodegradation"; Chemical Abstracts; vol. 108; 1988; p. 293, 108:10677p.

Portier et al.; "Continuous biodegradation and detoxification of chlorinated phenols using immobilized bacteria"; Chemical Abstracts; vol. 107; 1987; p. 189, 107:170091a.

Okafor; "Isolation of chitin from the shell of the cuttlefish, sepia officinalis"; Chemical Abstracts; vol. 63, 1965; col. 12035.

*Primary Examiner*—David M. Naff
*Attorney, Agent, or Firm*—Bacon & Thomas

[57] ABSTRACT

A suspension of a microorganism or a plurality of different microorganisms is added to a dispersion of β-chitin gel, and the resultant dispersion is molded and dried to produce an immobilized microorganism such as a film or membrane containing the microorganism. The β-chitin gel dispersion is prepared by isolating and grinding β-chitin from a source such as cuttlefish pen or squid pen, dispersing the ground β-chitin in water and forming a gel dispersion. In forming the gel dispersion, the dispersion of ground β-chitin is gelled and the gel is dispersed in water. Freeze-thawing may be used in gelling the dispersion of ground β-chitin. A film of the immobilized microorganism can be formed on an electrode to prepare a microorganism electrode.

9 Claims, 2 Drawing Sheets

MICROORGANISM IMMOBILIZATION IN A β-CHITIN CARRIER

BACKGROUND OF THE INVENTION i) Field of the Invention

The present invention relates to a carrier immobilized with a microorganism or a microorganism immobilized carrier and a producing method thereof, and more particularly to a microorganism immobilized carrier, where a microorganism is immobilized on β-chitin and a producing method thereof.

ii) Description of the Related Art

Recently, in the various industrial fields including the food industry, researches of a method for making a fermentation process continuous by using an immobilized microorganism obtained by immobilizing a microorganism on an insoluble high molecule polymer carrier have been developed. Also, researches relating to a microbial electrode composed of a combination of a carrier membrane immobilized with a microorganism and a variety of electrodes have actively been conducted.

When a microorganism is immobilized on a carrier in an industrial scale, the followings are required. That is, an immobilization operation is simple, the immobilized microorganism is kept to be stable for a long time, and the carrier to be used is porous and inexpensive. Further, when the microorganism immobilized carrier is used for a microbial electrode, it is necessary that a substrate permeability of the carrier is good and the carrier can be formed to a thin membrane.

However, in a conventional microbial immobilization, in many cases, a cross-linking processing or the like is required for the carrier, and a secondary deactivation can be unavoidable due to heat, organic solvents or the like in the cross-linking process.

On the other hand, chitin is a natural resource present in abundance, and it has proposed to use a chitin mold for a carrier for immobilizing an enzyme, as disclosed in Japanese Patent Publication Nos. Sho 56-00035, 53-10150.

In a conventional chitin mold preparation method, it is well-known to use the chitin isolated by treating the exoskeleton of the crustacea or insecta with hydrochloric acid and caustic soda, as disclosed in Japanese Patent Laid-Open Nos.Sho 61-53339, 61-64256, 61-111686, 61-129005 and 61-212302.

However, since the chitin obtained from the exoskeleton of the crustacea or insecta is an α-type chitin or α-chitin, the doping formation ability is bad, and as a result, the obtained carrier has only an insufficient strength. Further, when α-chitin is formed as a filmy carrier, a nonwoven fabric-like carrier is obtained and no thin membrane carrier can be formed. Hence, the α-chitin cannot be practically used for a carrier for immobilizing the microorganism.

Under such circumstances, in order to solve the above-described problems, the present inventors have earnestly made researches and have found that a chitin having a β-type structure or β-chitin obtained from cuttlefish pen (cuttlebone) among a lot of chitin raw materials, in particular, the β-chitin obtained from squid pen of the Teuthoidea or Sepioidea order in the *Mollusca phylum* possesses superior characteristics as a carrier, and by immobilizing a microorganism on the β-chitin, a microorganism immobilized carrier with high activity can be obtained to complete the present invention.

SUMMARY OF THE INVENTION

It is therefore an object of the present invention to provide a microorganism immobilized carrier obtained by immobilizing a microorganism on a β-chitin in view of the aforementioned problems of the prior art, which possesses high stability and can be prepared in a simple process.

It is another object of tile present invention to provide a method for producing a microorganism immobilized carrier having high stability in a simple process.

In accordance with one aspect of the present invention, there is provided a microorganism immobilized carrier comprising a β-chitin immobilized with a microorganism.

In accordance with another aspect of the present invention, there is provided a method for producing a microorganism immobilized carrier, comprising the steps of: dispersing a microorganism in a β-chitin dispersion; and molding the β-chitin dispersion dispersed with the microorganism into any form.

BRIEF DESCRIPTION OF THE DRAWINGS

These and other objects, features and advantages of the present invention will more fully appear from the following description of the preferred embodiments with reference to the accompanying drawings, in which.

DESCRIPTION OF THE PREFERRED EMBODIMENTS

Figure 1:
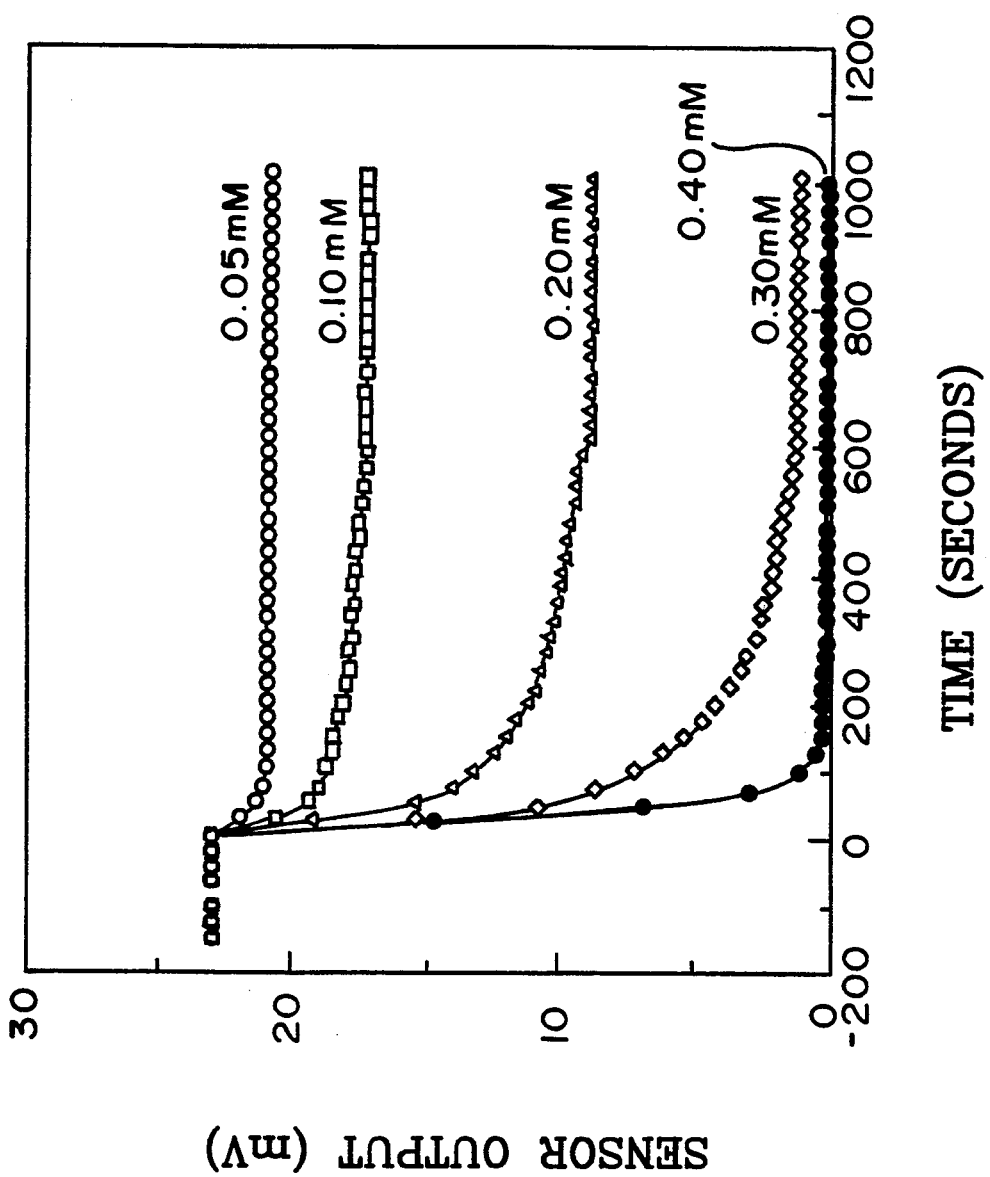
FIG. 1 is a graphical representation showing a variation of a sensor output amount in concentrations of glucose in a microorganism immobilized carrier according to the present invention.

The present invention will now be described in connection with its preferred embodiments with reference to the accompanying drawings.

According to the present invention, a β-chitin is isolated from cuttlefish pen, and the like.

In order to isolate the β-chitin from the cuttlefish pen, the cuttlefish pen is ground, and then the ground cuttlefish pen is treated with caustic soda and hydrochloric acid to remove protein and ash content. In an example using the cuttlefish pen as a raw material, the ground cuttlefish pen is treated by using approximately 1 N of caustic soda at a temperature of approximately 90° C. for approximately one hour and is then treated by using approximately 0.1 N of hydrochloric acid at room temperature for approximately one hour. The treated substance is dried to obtain the β-chitin.

In order to obtain the microorganism immobilized carrier according to the present invention, a sufficiently ground or milled β-chitin (preferably under 16 mesh) is suspended in water in a suitable concentration, i.e. approximately 5 to 20 weight % and is then vigorously stirred or subjected to a freezing-thawing treatment. Thus, the β-chitin absorbs water and its viscosity is raised to form the gel at last. The obtained gel is uniformly dispersed in water, and a predetermined amount of a microorganism suspension is uniformly added to the dispersion to obtain a β-chitin dispersion containing a microorganism. The β-chitin dispersion is dried and molded to obtain a β-chitin mold.

According to the present invention, the form of the microorganism immobilized carrier is not restricted in particular, and the carrier can be formed into membrane, particle or the like depending on its uses. For instance, the β-chitin dispersion containing the microorganism, obtained as described above, is placed on a filter for removing water, which is called papermaking, then, the obtained solid substance is dried to obtain a filmy microorganism immobilized carrier. The thus obtained filmy microorganism immobilized carrier can be used as a microbial electrode in combination with an electrode.

Further, according to the present invention, any microorganism can be immobilized on the β-chitin, and a combination of a plurality of microorganisms can also be immobilized.

In turn, in case that a microorganism immobilized carrier is prepared by using an β-chitin obtained from a crab and not from β-chitin, no chitin gel is obtained even when the aforementioned stirring or freezing-thawing treatment is carried out. Therefore, a chitin fiber is first prepared from the β-chitin and then by using the chitin fiber, a microorganism immobilized carrier is prepared. This means that β-chitin as a starting material can produce a filmy carrier, but it is a non-woven fabric-like carrier. This nonwoven fabric-like carrier is inferior in substrate permeability and strength and quite different from the filmy microorganism immobilized carrier according to the present invention.

As described above, tile microorganism immobilized carrier according to the present invention possesses high stability and can be prepared by a simple process. Although the present invention has been described in its preferred embodiments with reference to the accompanying drawings, it is readily understood that the present invention is not restricted to the preferred embodiments and that various changes and modifications can be made by those skilled in the art without departing from the spirit and scope of the present invention.

EXAMPLES

Now, the present invention will be described in detail with reference to the exemplary embodiments, and it should be understood that these embodiments are given only for illustration of the invention and are not intended to be limitative therefor.

Example 1

(1) 1 Kg of cuttlefish pen (cuttlebone) was ground by a feather mill (5 m/m, screen bath), and the ground substance was put into 1 N of NaOH solution to heat it at a temperature of 90° C. for 1 hour. After washing with water, the ground substance was immersed in 0.1 N HCl solution at room temperature for 1 hour. Then, after washing with water, the substance was heated in the 1 N NaOH solution at a temperature of 90° C. for 1 hour, and then after washing with water, the substance was dried in oven at a temperature of 50° C. for 5 hours to obtain 100 g of β-chitin.

(2) Next, the obtained β-chitin was ground, and water was added to the dried ground substance so as to be a 0.2 weight % concentration. The mixture liquid was vigorously stirred to raise the viscosity to form a paste gel. To 1.0 ml of the thus obtained gel, a solution obtained by suspending a microorganism obtained by a centrifugal separation of 10 ml of a colibacillus culture solution (OD=0.70) in a 1.0 ml of a physiological saline solution was added to perform a usual method of a water stream drop papermaking. The obtained solid was air-dried at room temperature for 2 hours to obtain a microorganism immobilized membrane.

Example 2

The microorganism immobilized membrane prepared in Example 1 was set on a cathode having a diameter of 3 mm of an oxygen electrode to form a microbial electrode. This microbial electrode was put in 20 ml of the air-saturated physiological saline solution maintained at a temperature of 37° C., and after an output current became a fixed value, 100 mM of glucose was added to the solution so as to be its final concentration of 0.05 to 0.4 mM to check the variation of the output.

Figure 2:
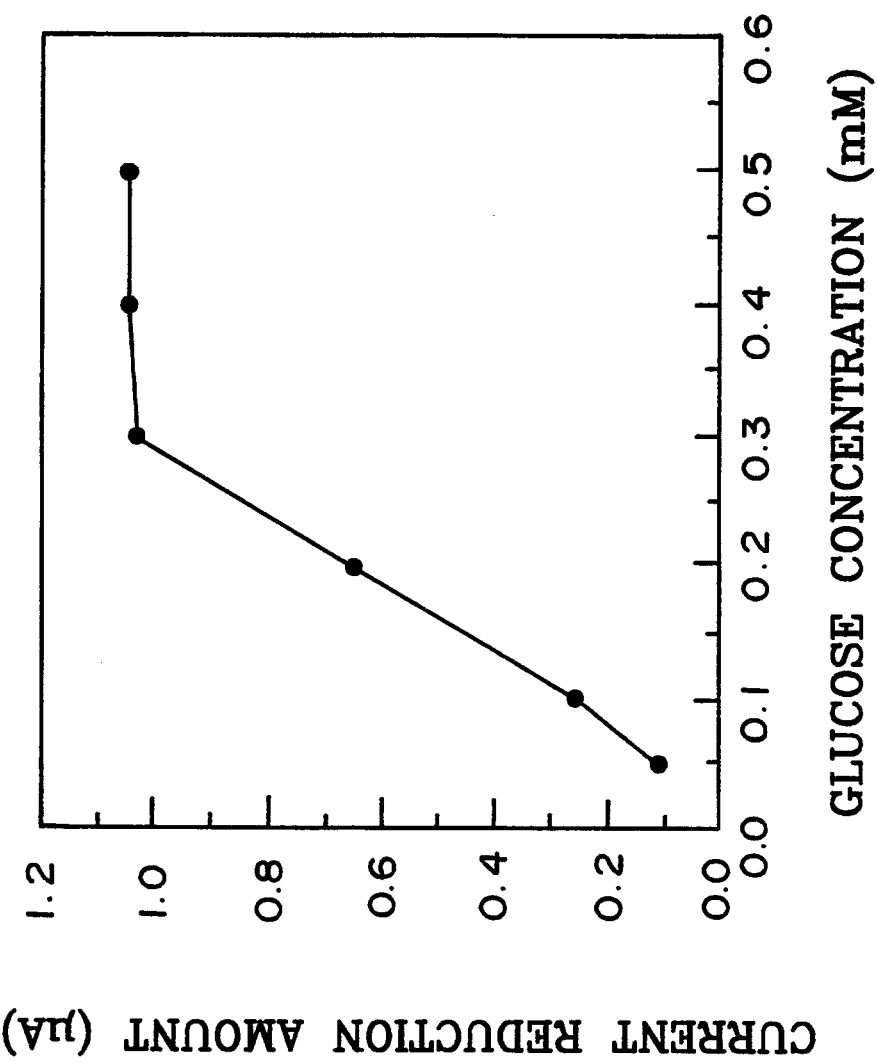
FIG. 2 is a graphical representation showing a relationship between a glucose concentration and a current reduction amount in a microorganism immobilized carrier according to the present invention.

The obtained results are shown in FIG. 1. As FIG. 1 shows, output current reduction was observed in any concentration right after the sample injection, and it was stabilized within approximately 400 seconds. The variation with respect to the glucose concentration was plotted to obtain FIG. 2, and a linear relationship was obtained in the glucose concentration of 0.05 to 0.3 mM.

What is claimed is:

1. A microorganism immobilized in a β-chitin containing carrier which is obtained by a process comprising the steps of:
   isolating β-chitin;
   grinding the isolated β-chitin;
   dispersing the ground β-chitin in water to form a β-chitin gel dispersion;
   adding a microorganism suspension to the β-chitin gel dispersion; and
   molding and drying the β-chitin gel and microorganism dispersion.

2. The microorganism immobilized in a carrier as claimed in claim 1 wherein the microorganism suspension contains a plurality of different microorganisms.

3. The microorganism immobilized in a carrier as claimed in claim 1 wherein the step of forming the β-chitin gel dispersion comprises vigorous stirring.

4. The microorganism immobilized in a carrier as claimed in claim 1 wherein the step of forming the β-chitin gel dispersion comprises freeze thawing.

5. The microorganism immobilized in a carrier as claimed in claim 1 wherein the β-chitin is isolated from cuttlefish pen.

6. The microorganism immobilized in a carrier as claimed in claim 1 wherein the β-chitin is isolated from squid pen.

7. The microorganism immobilized in a carrier as claimed in claim 1 wherein the molding and drying steps comprise placing the β-chitin gel and microorganism dispersion on a filter for removing water and drying the β-chitin gel and microorganism dispersion to form a film or membrane.

8. The microorganism immobilized in a carrier as claimed in claim 1 wherein the step of dispersing the ground β-chitin in water to form a β-chitin gel dispersion comprises dispersing the ground β-chitin in water to form a dispersion, gelling the β-chitin in the dispersion, and dispersing the gel in water to form a dispersion.

9. A microorganism electrode comprising an electrode and a microorganism immobilized in a β-chitin containing carrier which is obtained by a process comprising the steps of:
   isolating β-chitin;
   grinding the isolated β-chitin;
   dispersing the ground β-chitin in water to form a β-chitin gel dispersion;
   adding a microorganism suspension to the β-chitin gel dispersion; and
   molding and drying the β-chitin gel and microorganism dispersion.

* * * * *